United States Patent
Kim et al.

(10) Patent No.: US 10,046,307 B2
(45) Date of Patent: Aug. 14, 2018

(54) CATALYST FOR GLYCERIN DEHYDRATION, PREPARATION METHOD THEREFOR, AND ACROLEIN PREPARATION METHOD USING CATALYST

(71) Applicant: LG CHEM, LTD., Seoul (KR)

(72) Inventors: Ji Yeon Kim, Daejeon (KR); Jun Seon Choi, Daejeon (KR); Joo Young Cheon, Daejeon (KR); Wang Rae Joe, Daejeon (KR); Hye Jeong Ok, Daejeon (KR); Kyung Soo Kim, Daejeon (KR)

(73) Assignee: LG CHEM, LTD., Seoul (KR)

( * ) Notice: Subject to any disclaimer, the term of this patent is extended or adjusted under 35 U.S.C. 154(b) by 0 days.

(21) Appl. No.: 15/520,382

(22) PCT Filed: Dec. 8, 2015

(86) PCT No.: PCT/KR2015/013382
§ 371 (c)(1),
(2) Date: Apr. 19, 2017

(87) PCT Pub. No.: WO2016/099066
PCT Pub. Date: Jun. 23, 2016

(65) Prior Publication Data
US 2017/0304804 A1    Oct. 26, 2017

(30) Foreign Application Priority Data

Dec. 19, 2014  (KR) .................. 10-2014-0184903
Dec. 4, 2015   (KR) .................. 10-2015-0172428
Dec. 7, 2015   (KR) .................. 10-2015-0173228

(51) Int. Cl.
| | | |
|---|---|---|
| C07C 45/52 | (2006.01) | |
| B01J 37/00 | (2006.01) | |
| B01J 27/00 | (2006.01) | |
| B01J 21/06 | (2006.01) | |
| B01J 27/16 | (2006.01) | |
| B01J 27/18 | (2006.01) | |
| B01J 27/185 | (2006.01) | |
| B01J 27/188 | (2006.01) | |
| B01J 27/195 | (2006.01) | |
| B01J 37/03 | (2006.01) | |
| C07C 47/22 | (2006.01) | |

(52) U.S. Cl.
CPC ............. *B01J 21/066* (2013.01); *B01J 27/16* (2013.01); *B01J 27/1806* (2013.01); *B01J 27/1808* (2013.01); *B01J 27/188* (2013.01); *B01J 27/1817* (2013.01); *B01J 27/1853* (2013.01); *B01J 27/1856* (2013.01); *B01J 27/195* (2013.01); *B01J 37/033* (2013.01); *C07C 45/52* (2013.01); *C07C 47/22* (2013.01)

(58) Field of Classification Search
CPC .......... C07C 45/29; C07C 45/52; B01J 37/04; B01J 27/186

USPC .................. 568/486; 502/210, 219
See application file for complete search history.

(56) References Cited

U.S. PATENT DOCUMENTS

| | | | |
|---|---|---|---|
| 7,683,220 | B2 | 3/2010 | Matsunami et al. |
| 8,378,136 | B2 | 2/2013 | Dubois |
| 2008/0214384 | A1 | 9/2008 | Redlingshofer et al. |
| 2009/0118549 | A1 | 5/2009 | Matsunami et al. |
| 2010/0113838 | A1 | 5/2010 | Arita et al. |
| 2011/0028760 | A1 | 2/2011 | Dubois et al. |
| 2011/0082319 | A1 | 4/2011 | Dubois |
| 2011/0112330 | A1 | 5/2011 | Magatani et al. |
| 2013/0274095 | A1 | 10/2013 | Velasquez et al. |

FOREIGN PATENT DOCUMENTS

| | | |
|---|---|---|
| JP | 2007-268363 A | 10/2007 |
| JP | 2008-307521 A | 12/2008 |
| JP | 2010-516462 A | 5/2010 |
| KR | 10-2010-0057833 A | 6/2010 |
| KR | 10-2011-0011603 A | 2/2011 |
| KR | 10-2011-0016969 A | 2/2011 |
| KR | 10-2011-0077007 A | 7/2011 |
| KR | 10-2013-0103639 A | 9/2013 |
| WO | 2009-029540 A2 | 3/2009 |
| WO | 2013-008279 A1 | 1/2013 |

OTHER PUBLICATIONS

Chai et al, "Sustainable Production of Acrolein Preparation and Charaterization of Zirconia-supported 12-Tungstosphoric Acid Catalyst for Gas-Phase Dehydration of Glycerol," Applied Catalysis A: General, 2009, vol. 353, pp. 213-222.
Katryniok et al, "Recent Developments in the Field of Catalytic Dehydration of Glycerol to Acrolein," ACS Catalysis, 2013, vol. 3, pp. 1819-1834.
Rajan et al, "Vapour Phase Hydration of Glycerol over VPO Catalyst supported on Zirconium Phosphate," Catalysis Science & Technology, Oct. 9, 2013, vol. 4, pp. 81-92.
Gan et al. "Gas Phase Dehydration of Glycerol to ACrolein Catalyzed by Zirconium Phosphate," Chinese Journal of catalysis, Jul. 20, 2014, vol. 35, pp. 1148-1156.
Katryniok et al, "Towards the Sustainable Production of Acrolein by Glycerol Dehydration," Chem Sus Chem, 2009, vol. 2, pp. 719-730.
Talebian-Kiakalaieh et al, "Glycerol for renewable acrolein production by catalytic dehydration," Renewable and Sustainable Energy Reviews, 2014, vol. 40, pp. 28-59.
Znaiguia et al, "Toward longer life catalysts for dehydration of glycerol to acrolein," Microporous and Microporous Materials, 2014, vol. 196, pp. 97-103.
Rao et al, "Porous zirconium phosphate supported tungsten oxide solid acid catalysts for the vapour phase dehydration of glycerol," Journal of Molecular Cata;ysis A: Chemical, 2014, vol. 395, pp. 486-493.

*Primary Examiner* — Sikarl Witherspoon
(74) *Attorney, Agent, or Firm* — Dentons US LLP

(57) ABSTRACT

The present invention relates to: a catalyst for glycerin dehydration; a preparation method therefor; and an acrolein preparation method using the catalyst. According to one embodiment of the present invention, the catalyst is used in glycerin dehydration so as to exhibit high catalytic activity, a high yield and high acrolein selectivity, and has a characteristic in which carbon is not readily deposited, thereby having a long lifetime compared with that of a conventional catalyst.

11 Claims, No Drawings

CATALYST FOR GLYCERIN DEHYDRATION, PREPARATION METHOD THEREFOR, AND ACROLEIN PREPARATION METHOD USING CATALYST

CROSS-REFERENCE TO RELATED APPLICATION(S)

This application is a National Stage Application of International Application No. PCT/KR2015/013382, filed on Dec. 8, 2015, which claims priority to and the benefit of priority of Korean Patent Application Nos. 10-2014-0184903, filed on Dec. 19, 2014; 10-2015-0172428, filed on Dec. 4, 2015; and 10-2015-0173228, filed on Dec. 7, 2015, all of which are hereby incorporated by reference in their entirety for all purposes as if fully set forth herein.

TECHNICAL FIELD

The present invention relates to a catalyst for dehydration of glycerin, a preparation method thereof, and a preparation method of acrolein using the catalyst.

BACKGROUND OF THE INVENTION

Acrolein is a simple unsaturated aldehyde compound which includes incomplete reactive groups to have high reactivity, and is used as a major intermediate for synthesis of numerous chemicals. In particular, acrolein has been widely used as an intermediate for syntheses of acrylic acids, acrylic acid esters, superabsorbent polymers, animal feed supplements, or food supplements.

Such acrolein has been mainly prepared by selective gas-phase oxidation of a starting material, propylene, which is obtained during petroleum cracking with atmospheric oxygen. However, as fossil fuels have been reduced and environmental problems such as the greenhouse effect have emerged, many studies have been conducted to develop a method of preparing acrolein using non-fossil fuel-based renewable materials.

Therefore, glycerin, which is a natural by-product obtained from biodiesel production, has received much attention as a raw material for acrolein preparation. In particular, the growth of biodiesel production increases the glycerin market, and industrial application of glycerin has been studied due to its low price.

For example, a method of obtaining a mixture of acrolein and acrylic acid by dehydration of glycerin in the presence of a catalyst is known. The dehydration of glycerin is performed by gas-phase oxidation in the presence of a catalyst, and use of the catalyst is essential.

However, the dehydration of glycerin has a problem of depositing carbon on the catalyst and inactivating the catalyst as the reaction proceeds. Accordingly, efforts for developing a catalyst increased in lifespan by preventing carbon deposition are going on.

DETAILS OF THE INVENTION

Objects of the Invention

The present invention provides a catalyst for dehydration of glycerin, which has an increased lifespan by preventing carbon deposition during the dehydration of glycerin and shows high acrolein selectivity and efficiency, and a preparation method thereof.

In addition, the present invention provides a preparation method of acrolein using the catalyst.

Means for Achieving the Object

According to one embodiment, the present invention provides a catalyst for dehydration of glycerin represented by the following Chemical Formula 1:

$$Zr_xA_n(H_yPO_m)_z \qquad \text{[Chemical Formula 1]}$$

In Chemical Formula 1, A is one or more atoms selected from the group consisting of B, W, V, Ca, K, Mg, Sr, Ag, Ni, Zn, Fe, Sn, and Nb; and x, n, m, y, and z represent ratios of atoms or atom groups, wherein x is 0.1 to 6, n is 0.01 to 8, y is 0.1 to 10, m is 1 to 5, and z is 1 to 12.

For example, n may be 0.01 to 0.3, m may be 4, x may be 0.5 to 1, y may be 1 to 3, and z may be 1 to 5.

Concretely, the catalyst represented by Chemical Formula 1 may be a compound represented by any one of Chemical Formulae 2 to 4:

$$Zr_xA^1_{n1}(H_yPO_4)_z \qquad \text{[Chemical Formula 2]}$$

In Chemical Formula 2, x is 0.5 to 1, $A^1$ is W or Zn, n1 is 0.01 to 0.3, y is 1 to 3, and z is 1 to 5.

$$Zr_xA^2_{n2}W_{n3}(H_yPO_4)_z \qquad \text{[Chemical Formula 3]}$$

In Chemical Formula 3, x is 0.5 to 1, $A^2$ is B, V, Ca, K, Mg, Ag, Zn, Fe, or Nb, y is 1 to 3, z is 1 to 5, and n2 and n3 are independently a rational number between 0.001 to 0.2 and the sum of n2 and n3 is 0.01 to 0.3.

$$Zr_xA^3_{n4}A^4_{n5}A^5_{n6}(H_yPO_4)_z \qquad \text{[Chemical Formula 4]}$$

In Chemical Formula 4, x is 0.5 to 1, $A^3$ to $A^5$ are independently W, Zn, or Fe, y is 1 to 3, z is 1 to 5, and n4 to n6 are independently a rational number between 0.001 to 0.2 and the sum of n4, n5, and n6 is 0.01 to 0.3.

More specifically, the catalyst represented by Chemical Formula 1 may be $ZrB_{0.1}W_{0.1}(H_yPO_4)_{2.2}$, $Zr_{0.9}Fe_{0.1}W_{0.1}Zn_{0.02}(H_yPO_4)_2$, $ZrZn_{0.1}(H_yPO_4)_2$, $Zr_{0.9}Ag_{0.1}W_{0.1}(H_yPO_4)_2$, or $Zr_{0.9}Ca_{0.01}W_{0.1}(H_yPO_4)_2$, and said y may be 1 to 3.

Meanwhile, according to another embodiment, the present invention provides a preparation method of a catalyst for dehydration of glycerin, including the steps of: mixing one or more precursors selected from the group consisting of the precursors of B, W, V, Ca, K, Mg, Sr, Ag, Ni, Zn, Fe, Sn, and Nb, a zirconium precursor, and a phosphate compound, and precipitating the catalyst represented by Chemical Formula 1 therefrom.

The step of precipitating the catalyst may include the process of stirring the mixture including one or more precursors selected from the group consisting of the precursors of B, W, V, Ca, K, Mg, Sr, Ag, Ni, Zn, Fe, Sn, and Nb, a zirconium precursor, and a phosphate compound at the temperature of 25 to 200° C. And, the mixture may be stirred for about 3 to 48 hrs.

The preparation method may further include the step of washing the precipitated catalyst with an alcohol, after the precipitation step.

In addition, according to still another embodiment, the present invention provides a preparation method of acrolein, including the step of dehydrating glycerin in the presence of the catalyst for dehydration of glycerin.

Effects of the Invention

The catalyst according to the present invention shows high catalytic activity, high yield, and high acrolein selectivity when it is used for dehydration of glycerin, and it has an increased lifespan than existing catalysts because it is hard to be deposited by carbon.

DETAILED DESCRIPTION OF THE EMBODIMENT

Hereinafter, a catalyst for dehydration of glycerin according to a concrete embodiment, a preparation method thereof, and a preparation method of acrolein using the catalyst are explained.

According to one embodiment of the invention, a catalyst for dehydration of glycerin represented by the following Chemical Formula 1 is provided.

$$Zr_xA_n(H_yPO_m)_z$$ [Chemical Formula 1]

In Chemical Formula 1, A is one or more atoms selected from the group consisting of B, W, V, Ca, K, Mg, Sr, Ag, Ni, Zn, Fe, Sn, and Nb; and x, n, m, y, and z represent ratio of atoms or atom groups, wherein x is 0.1 to 6, n is 0.01 to 8, y is 0.1 to 10, m is 1 to 5, and z is 1 to 12.

Acrolein can be obtained by dehydrating glycerin in the presence of an acid catalyst. At this time, it is known that the production efficiency of acrolein is good when the catalyst having lots of Brønsted acid sites rather than Lewis acid sites is used as the acid catalyst. However, the acid catalyst having lots of Brønsted acid sites has a problem of that the acid catalyst is deposited by carbon and is easily inactivated.

The catalyst represented by Chemical Formula 1 designed for resolving this problem is characterized in that it has Brønsted acid sites but it is not easily inactivated in dehydration of glycerin. Furthermore, since the catalyst of Chemical Formula 1 has Brønsted acid sites, it may be superior in acrolein yield and catalytic activity to zirconium phosphate, known for excellent catalytic activity.

For example, in order to improve the acrolein yield and the catalytic activity in comparison to existing zirconium, n may be 0.01 to 0.3, m may be 4, x may be 0.5 to 1, y may be 1 to 3, and z may be 1 to 5 in Chemical Formula 1.

More specifically, the catalyst of Chemical Formula 1 may be the compounds represented by Chemical Formulae 2 to 4.

$$Zr_xA^1_{n1}(H_yPO_4)_z$$ [Chemical Formula 2]

In Chemical Formula 2, x is 0.5 to 1, A1 is W or Zn, n1 is 0.01 to 0.3, y is 1 to 3, and z is 1 to 5.

$$Zr_xA^2_{n2}W_{n3}(H_yPO_4)_z$$ [Chemical Formula 3]

In Chemical Formula 3, x is 0.5 to 1, $A^2$ is B, V, Ca, K, Mg, Ag, Zn, Fe, or Nb, y is 1 to 3, z is 1 to 5, and n2 and n3 are independently a rational number between 0.001 to 0.2 and the sum of n2 and n3 is 0.01 to 0.3.

$$Zr_xA^3_{n4}A^4_{n5}A^3_{n6}(H_yPO_4)_z$$ [Chemical Formula 4]

In Chemical Formula 4, x is 0.5 to 1, $A^3$ to $A^5$ are independently W, Zn, or Fe, y is 1 to 3, z is 1 to 5, and n4 to n6 are independently a rational number between 0.001 to 0.2 and the sum of n4, n5, and n6 is 0.01 to 0.3.

Particularly, referring to Examples and Comparative Examples disclosed below, $ZrB_{0.1}W_{0.1}(H_yPO_4)_{2.2}$, $Zn_{0.9}Fe_{0.1}W_{0.1}Zn_{0.02}(H_yPO_4)_2$, $ZrZn_{0.1}(H_yPO_4)_2$, $Zr_{0.9}Ag_{0.1}W_{0.1}(H_yPO_4)_2$, and $Zr_{0.9}Ca_{0.01}W_{0.1}(H_yPO_4)_2$ in the catalyst of Chemical Formula 1 can achieve the acrolein yield of 35% or more.

Meanwhile, according to another embodiment of the invention, a preparation method of the catalyst represented by Chemical Formula 1 using a precipitation method is provided. Specifically, the preparation method of the catalyst represented by Chemical Formula 1 includes the steps of mixing one or more precursors (hereinafter, precursor of atom A) selected from the group consisting of the precursors of B, W, V, Ca, K, Mg, Sr, Ag, Ni, Zn, Fe, Sn, and Nb, a zirconium precursor, and a phosphate compound, and precipitating the catalyst of Chemical Formula 1 therefrom.

The catalyst of Chemical Formula 1 can be obtained as a precipitate when the precursor of atom A, the zirconium precursor, and the phosphate compound are mixed, and thus the mixing method of the precursor of atom A, the zirconium precursor, and the phosphate compound is not limited particularly. For non-restrictive example, the precursors may be successively put in a reactor one by one or at once, and mixed. Most of all, in the case of putting the zirconium precursor, the precursor of atom A, and the phosphate compound successively in the reactor, the precursors are well dissolved because the phosphate compound is added after the zirconium precursor and the precursor of atom A are completely dissolved, and the catalyst yield can be increased because a stable crystal structure can be formed more easily.

In the step of precipitating the catalyst, the amount of the catalyst formed may be increased by putting a solvent in the reactor at first and adding the precursors thereto with stirring, or by putting a part of the precursors in the reactor and adding the rest of the precursors thereto with stirring, or by putting all of the precursors in the reactor and stirring the mixture of the precursors. For example, it is possible that a solvent such as water and the like is put in the reactor at first and the precursors are successively or simultaneously put in the reactor with stirring the solvent. And, for another example, it is possible that a part of the precursors are put in the reactor at first and the rest of the precursors are successively or simultaneously added thereto with stirring the same. And, for still another example, it is possible that all of the precursors are successively or simultaneously put in the reactor for preparing a mixture and the mixture is stirred.

In all of above cases, the mixture of the precursors may be stirred even after all of the precursors are put in the reactor. Particularly, the stirring of the mixture may be carried out at the temperature of about 25 to 200° C. for making the bond between metals more easy.

Furthermore, the stirring may be carried out for a sufficient time to mix all of the precursors well for generating plenty of precipitates. For example, the stirring may be carried out for about 3 to 48 hrs.

As the precursor used in the preparation method, various precursors known in the art to which the present invention pertains may be used. For non-restrictive example, zirconyl chloride, zirconyl bromide, zirconyl iodide, zirconyl nitrate, and so on may be used as the zirconium precursor. And, an oxide of metal A, a hydroxide of metal A, a nitrate of metal A, an oxalate of metal A, a phosphate of metal A, a halide of metal A, and so on may be used as the precursor of atom A. For example, $H_3BO_3$ and so on may be used as a boron precursor, $Zn(NO_3)_2$ and so on may be used as a zinc precursor, $Fe(NO_3)_3$ and so on may be used as an iron precursor, $NH_4VO_3$ and so on may be used as a vanadium precursor, $CaHPO_4$, $Ca(NO_3)_2$, and so on may be used as a calcium precursor, $MgHPO_4$, $Mg(NO_3)_2$, and so on may be used as a magnesium precursor, $KNO_3$ and so on may be used as a potassium precursor, $AgNO_3$ and so on may be used as a silver precursor, $C_4H_4NNbO_9$ and so on may be used as a niobium precursor, and ammonium metatungstate, ammonium paratungstate, tungstic acid, tungsten blue oxide, tungsten trioxide, and so on may be used as a tungsten precursor. Here, 2 or more precursors may be used as the precursor of atom A, and, for non-restrictive example, a boron precursor and a tungsten precursor may be used together. And, phosphoric acid or a phosphate in which one or more protons of phosphoric acid are substituted by cations of group 1 element, group 2 element, or group 13 element or by an ammonium cation may be used as the phosphate compound. The precursors may be anhydrides or hydrates. And, the precursors may be used in a proper content according to the ratio of atoms and atomic groups of Chemical Formula 1.

In the step of precipitating the catalyst, a proper solvent may be used for uniform mixing of the precursors. The solvent is not limited particularly, and water and the like may be used as a non-restrictive example.

The preparation method may further include the step of washing the precipitated catalyst obtained in the step of precipitating the catalyst with an alcohol. The precipitate obtained by a precipitation method of metal compound is generally washed with water, but one embodiment of the present invention can prepare the catalyst having more wide surface area by washing the precipitate with an alcohol. The catalyst having wide surface area can show more excellent catalytic activity and acrolein selectivity in the dehydration of glycerin.

The alcohol which can be used in the washing step may be a C1-C10 alkyl alcohol such as methanol, ethanol, propanol, butanol, pentanol, hexanol, and so on.

The preparation method may further include a step which is commonly used in the art to which the present invention pertains, in addition to the steps disclosed above.

Meanwhile, according to another embodiment of the invention, a preparation method of acrolein, including the step of dehydrating glycerin in the presence of the catalyst for dehydration of glycerin is provided The preparation method of acrolein, for example, may provide acrolein by carrying out the dehydration reaction of glycerin in a continuous flow gas-phase reacting system in which the catalyst exits.

Glycerin or a glycerin aqueous solution may be used as a reactant of the preparation method. And, an inert gas or a gas mixture of an inert gas and air or oxygen may be used as a carrier gas for the reactant.

The dehydration reaction of glycerin may be carried out under the temperature of 220 to 400° C., or 220 to 335° C. Since the dehydration reaction of glycerin is an endothermic reaction, sufficient reaction speed cannot be secured when the reaction temperature is too low. And, the selectivity to the polymerization reaction of glycerin may increase when the temperature is low. Therefore, the dehydration reaction of glycerin may be carried out at the temperature of 220° C. or more. However, since the selectivity to by-products such as 1-hydroxyacetone (acetol), an allyl alcohol, and so on may increase when the reaction temperature is too high, the dehydration reaction of glycerin may be carried out at the temperature of 400° C. or less.

And, the dehydration reaction of glycerin may be carried out under the weight hourly space velocity of glycerin to the catalyst of 1.0 to 200.0 mmol/hr·$g_{cat}$. Namely, in order to secure the productivity of acrolein, the weight hourly space velocity of glycerin to the catalyst may be adjusted to 1.0 mmol/hr·$g_{cat}$ or more. However, if the weight hourly space velocity of glycerin is too high, the caulking deposition due to the reaction by-product occurs fast and the reaction efficiency may decrease. Therefore, the weight hourly space velocity of glycerin to the catalyst may be adjusted to 200.0 mmol/hr·$g_{cat}$ or less.

Hereinafter, function and effect of the present invention will be explained in more detail with reference to the following examples. However, these examples are only to illustrate the invention, and the scope of the invention is not limited thereto.

Preparation Example 1: Preparation of the Catalyst for Dehydration of Glycerin

An aqueous solution was prepared by adding 12.208 g of $ZrOCl_2$, a zirconium precursor, to 150 mL of distilled water. 0.234 g of $H_3BO_3$, a boron precursor, and 0.933 g of $H_{26}N_6O_{40}W_{12}$, a tungsten precursor, were added to the aqueous solution and the mixture was stirred for about 30 mins to 1 hr. And, after preparing another aqueous solution by adding 9.585 g of $NH_4H_2PO_4$, a phosphate compound, to 150 mL of distilled water, the phosphate aqueous solution was added to the zirconium aqueous solution prepared above and the mixture was stirred overnight at the temperature of about 95° C.

And then, $ZrB_{0.1}W_{0.1}(H_yPO_4)_{2.2}$, the catalyst for dehydration of glycerin, was obtained after washing the precipitate settled from the aqueous solution with ethanol.

Preparation Example 2: Preparation of the Catalyst for Dehydration of Glycerin $Zr_{0.775}B_{0.1}W_{0.1}(H_yPO_4)_2$, the catalyst for dehydration of glycerin, was obtained according to the same method as in Preparation Example 1, except that 9.461 g of $ZrOCl_2$ was used.

Preparation Example 3: Preparation of the Catalyst for Dehydration of Glycerin

An aqueous solution was prepared by adding 12.208 g of $ZrOCl_2$, a zirconium precursor, to 150 mL of distilled water. 0.225 g of $Zn(NO_3)_2·6H_2O$, a zinc precursor, and 0.933 g of $H_{26}N_6O_{40}W_{12}$, a tungsten precursor, were added to the aqueous solution and the mixture was stirred for about 30 mins to 1 hr. And, after preparing another aqueous solution by adding 8.714 g of $NH_4H_2PO_4$, a phosphate compound, to 150 mL of distilled water, the phosphate aqueous solution was added to the zirconium aqueous solution prepared above and the mixture was stirred overnight at the temperature of about 95° C.

And then, $ZrZn_{0.02}W_{0.1}(H_yPO_4)_2$, the catalyst for dehydration of glycerin, was obtained after washing the precipitate settled from the aqueous solution with ethanol.

Preparation Example 4: Preparation of the Catalyst for Dehydration of Glycerin

An aqueous solution was prepared by adding 10.986 g of $ZrOCl_2$, a zirconium precursor, to 150 mL of distilled water. 1.54 g of $Fe(NO_3)_3·9H_2O$, a iron precursor, and 0.933 g of $H_{26}N_6O_{40}W_{12}$, a tungsten precursor, were added to the aqueous solution and the mixture was stirred for about 30 mins to 1 hr. And, after preparing another aqueous solution by adding 9.585 g of $NH_4H_2PO_4$, a phosphate compound, to 150 mL of distilled water, the phosphate aqueous solution was added to the zirconium aqueous solution prepared above and the mixture was stirred overnight at the temperature of about 95° C.

And then, $Zr_{0.9}Fe_{0.1}W_{0.1}(H_yPO_4)_2$, the catalyst for dehydration of glycerin, was obtained after washing the precipitate settled from the aqueous solution with ethanol.

Preparation Example 5: Preparation of the Catalyst for Dehydration of Glycerin An aqueous solution was prepared by adding 10.986 g of $ZrOCl_2$, a zirconium precursor, to 150 mL of distilled water. 0.448 g of $NH_4VO_3$, a vanadium precursor, and 0.933 g of $H_{26}N_6O_{40}W_{12}$, a tungsten precursor, were added to the aqueous solution and the mixture was stirred for about 30 mins to 1 hr. And, after preparing another aqueous solution by adding 8.714 g of $NH_4H_2PO_4$, a phosphate compound, to 150 mL of distilled water, the phosphate aqueous solution was added to the zirconium aqueous solution prepared above and the mixture was stirred overnight at the temperature of about 95° C.

And then, $Zr_{0.9}V_{0.1}W_{0.1}(H_yPO_4)_2$, the catalyst for dehydration of glycerin, was obtained after washing the precipitate settled from the aqueous solution with ethanol.

Preparation Example 6: Preparation of the Catalyst for Dehydration of Glycerin An aqueous solution was prepared by adding 12.208 g of $ZrOCl_2$, a zirconium precursor, to 150 mL of distilled water. 2.799 g of $H_{26}N_6O_{40}W_{12}$, a tungsten precursor, was added to the aqueous solution and the mixture was stirred for about 30 mins to 1 hr. And, after preparing another aqueous solution by adding 8.714 g of $NH_4H_2PO_4$, a phosphate compound, to 150 mL of distilled water, the phosphate aqueous solution was added to the zirconium aqueous solution prepared above and the mixture was stirred overnight at the temperature of about 95° C.

And then, $ZrW_{0.3}(H_yPO_4)_2$, the catalyst for dehydration of glycerin, was obtained after washing the precipitate settled from the aqueous solution with ethanol.

Preparation Example 7: Preparation of the Catalyst for Dehydration of Glycerin An aqueous solution was prepared by adding 10.986 g of $ZrOCl_2$, a zirconium precursor, to 150 mL of distilled water. 1.54 g of $Fe(NO_3)_3 \cdot 9H_2O$, an iron precursor, 0.225 g of $Zn(NO_3)_2 \cdot 6H_2O$, a zinc precursor, and 0.933 g of $H_{26}N_6O_{40}W_{12}$, a tungsten precursor, were added to the aqueous solution and the mixture was stirred for about 30 mins to 1 hr. And, after preparing another aqueous solution by adding 8.714 g of $NH_4H_2PO_4$, a phosphate compound, to 150 mL of distilled water, the phosphate aqueous solution was added to the zirconium aqueous solution prepared above and the mixture was stirred overnight at the temperature of about 95° C.

And then, $Zr_{0.9}Fe_{0.1}W_{0.1}Zn_{0.02}(H_yPO_4)_2$, the catalyst for dehydration of glycerin, was obtained after washing the precipitate settled from the aqueous solution with ethanol.

Preparation Example 8: Preparation of the Catalyst for Dehydration of Glycerin An aqueous solution was prepared by adding 12.208 g of $ZrOCl_2$, a zirconium precursor, to 150 mL of distilled water. 1.24 g of $Zn(NO_3)_2 \cdot 6H_2O$, a zinc precursor, was added to the aqueous solution and the mixture was stirred for about 30 mins to 1 hr. And, after preparing another aqueous solution by adding 8.714 g of $NH_4H_2PO_4$, a phosphate compound, to 150 mL of distilled water, the phosphate aqueous solution was added to the zirconium aqueous solution prepared above and the mixture was stirred overnight at the temperature of about 95° C.

And then, $ZrZn_{0.1}(H_yPO_4)_2$, the catalyst for dehydration of glycerin, was obtained after washing the precipitate settled from the aqueous solution with ethanol.

Preparation Example 9: Preparation of the Catalyst for Dehydration of Glycerin An aqueous solution was prepared by adding 10.986 g of $ZrOCl_2$, a zirconium precursor, to 150 mL of distilled water. 0.643 g of $AgNO_3$, a silver precursor, and 0.933 g of $H_{26}N_6O_{40}W_{12}$, a tungsten precursor, were added to the aqueous solution and the mixture was stirred for about 30 mins to 1 hr. And, after preparing another aqueous solution by adding 8.714 g of $NH_4H_2PO_4$, a phosphate compound, to 150 mL of distilled water, the phosphate aqueous solution was added to the zirconium aqueous solution prepared above and the mixture was stirred overnight at the temperature of about 95° C.

And then, $Zr_{0.9}Ag_{0.1}W_{0.1}(H_yPO_4)_2$, the catalyst for dehydration of glycerin, was obtained after washing the precipitate settled from the aqueous solution with ethanol.

Preparation Example 10: Preparation of the Catalyst for Dehydration of Glycerin An aqueous solution was prepared by adding 10.986 g of $ZrOCl_2$, a zirconium precursor, to 150 mL of distilled water. 0.904 g of $Ca(NO_3)_2 \cdot 4H_2O$, a calcium precursor, and 0.933 g of $H_{26}N_6O_{40}W_{12}$, a tungsten precursor, were added to the aqueous solution and the mixture was stirred for about 30 mins to 1 hr. And, after preparing another aqueous solution by adding 8.714 g of $NH_4H_2PO_4$, a phosphate compound, to 150 mL of distilled water, the phosphate aqueous solution was added to the zirconium aqueous solution prepared above and the mixture was stirred overnight at the temperature of about 95° C.

And then, $Zr_{0.9}Ca_{0.1}W_{0.1}(H_yPO_4)_2$, the catalyst for dehydration of glycerin, was obtained after washing the precipitate settled from the aqueous solution with ethanol.

Preparation Example 11: Preparation of the Catalyst for Dehydration of Glycerin An aqueous solution was prepared by adding 10.986 g of $ZrOCl_2$, a zirconium precursor, to 150 mL of distilled water. 1.147 g of $C_4H_4NNbO_9 \cdot xH_2O$, a niobium precursor, and 0.933 g of $H_{26}N_6O_{40}W_{12}$, a tungsten precursor, were added to the aqueous solution and the mixture was stirred for about 30 mins to 1 hr. And, after preparing another aqueous solution by adding 8.714 g of $NH_4H_2PO_4$, a phosphate compound, to 150 mL of distilled water, the phosphate aqueous solution was added to the zirconium aqueous solution prepared above and the mixture was stirred overnight at the temperature of about 95° C.

And then, $Zr_{0.9}Nb_{0.1}W_{0.1}(H_yPO_4)_2$, the catalyst for dehydration of glycerin, was obtained after washing the precipitate settled from the aqueous solution with ethanol.

Preparation Example 12: Preparation of the Catalyst for Dehydration of Glycerin An aqueous solution was prepared by adding 10.986 g of $ZrOCl_2$, a zirconium precursor, to 150 mL of distilled water. 0.971 g of $Mg(NO_3)_2 \cdot 6H_2O$, a magnesium precursor, and 0.933 g of $H_{26}N_6O_{40}W_{12}$, a tungsten precursor, were added to the aqueous solution and the mixture was stirred for about 30 mins to 1 hr. And, after preparing another aqueous solution by adding 8.714 g of $NH_4H_2PO_4$, a phosphate compound, to 150 mL of distilled water, the phosphate aqueous solution was added to the zirconium aqueous solution prepared above and the mixture was stirred overnight at the temperature of about 95° C.

And then, $Zr_{0.9}Mg_{0.1}W_{0.1}(H_yPO_4)_2$, the catalyst for dehydration of glycerin, was obtained after washing the precipitate settled from the aqueous solution with ethanol.

Preparation Example 13: Preparation of the Catalyst for Dehydration of Glycerin $Zr_{0.9}C_{0.01}W_{0.1}(H_yPO_4)_2$, the catalyst for dehydration of glycerin, was obtained according to the same method as in Preparation Example 10, except that 0.0904 g of Ca$(NO_3)_2 \cdot 4H_2O$, a calcium precursor, was used.

Preparation Example 14: Preparation of the Catalyst for Dehydration of Glycerin

An aqueous solution was prepared by adding 10.986 g of $ZrOCl_2$, a zirconium precursor, to 150 mL of distilled water. 0.0383 g of $KNO_3$, a potassium precursor, and 0.933 g of $H_{26}N_6O_{40}W_{12}$, a tungsten precursor, were added to the aqueous solution and the mixture was stirred for about 30 mins to 1 hr. And, after preparing another aqueous solution by adding 8.714 g of $NH_4H_2PO_4$, a phosphate compound, to 150 mL of distilled water, the phosphate aqueous solution was added to the zirconium aqueous solution prepared above and the mixture was stirred overnight at the temperature of about 95° C.

And then, $Zr_{0.9}K_{0.01}W_{0.1}(H_yPO_4)_2$, the catalyst for dehydration of glycerin, was obtained after washing the precipitate settled from the aqueous solution with ethanol.

Example 1: Dehydration Reaction of Glycerin

The preparation of acrolein by dehydration of glycerin was carried out by using a continuous flow fixed bed reactor. After installing the continuous flow fixed bed reactor in an electric furnace, 0.3 g of the catalyst prepared in Preparation Example 1 was put in the reactor. After elevating the temperature of the reactor to about 280° C. with flowing nitrogen and air, carrier gas, respectively with the velocity of 10 mL/min, the temperature was maintained for a period of time for maintaining the steady state of the reaction line.

Subsequently, glycerin aqueous solution (28.08 wt % in $H_2O$; 7.1 mol %) was introduced to the reactor with the velocity of 10.5 mL/hr, in order that the weight hourly space velocity to the catalyst became 113.03 mmol/hr·$g_{cat}$, and the dehydration reaction of glycerin was carried out.

The dehydration reaction of glycerin was carried out at the temperature of about 269° C. under atmospheric pressure for about 26 hrs, and the product obtained after the reaction included not only acrolein, the main product, but also by-products such as hydroxyacetone (acetol) and allyl alcohol and unreacted glycerin. During the reaction proceeded, the reaction product was sampled for 10 mins once an hour and analyzed by gas chromatography at regular intervals.

Examples 2 to 8 and Comparative Example 1: Dehydration Reaction of Glycerin

The dehydration reaction of glycerin was carried out according to the same method as in Example 1, except that the catalyst, the carrier gas, the reaction temperature, or the reaction time were changed as disclosed in the following Table 1.

TABLE 1

| | Catalyst | Carrier Gas | Reaction Temperature [° C.] | Reaction Time [hr] |
|---|---|---|---|---|
| Example 1 | $ZrB_{0.1}W_{0.1}(H_yPO_4)_{2.2}$ of Preparation Example 1 | $N_2$ + air | 269 | 26 |
| Example 2 | $Zr_{0.775}B_{0.1}W_{0.1}(H_yPO_4)_2$ of Preparation Example 2 | $N_2$ + air | 270 | 5 |
| Example 3 | $ZrZn_{0.02}W_{0.1}(H_yPO_4)_2$ of Preparation Example 3 | $N_2$ + air | 265 | 5 |
| Example 4 | $Zr_{0.9}Fe_{0.1}W_{0.1}(H_yPO_4)_2$ of Preparation Example 4 | $N_2$ + air | 269 | 5 |
| Example 5 | $Zr_{0.9}V_{0.1}W_{0.1}(H_yPO_4)_2$ of Preparation Example 5 | $N_2$ + air | 269 | 5 |
| Example 6 | $ZrW_{0.3}(H_yPO_4)_2$ of Preparation Example 6 | $N_2$ + air | 268 | 5 |
| Example 7 | $Zr_{0.9}Fe_{0.1}W_{0.1}Zn_{0.02}(H_yPO_4)_2$ of Preparation Example 7 | $N_2$ + air | 269 | 5 |
| Example 8 | $ZrZn_{0.1}(H_yPO_4)_2$ of Preparation Example 8 | $N_2$ + air | 269 | 29 |
| Comparative Example 1 | 11.8 wt % $BPO_4/SiO_2$ | $N_2$ | 263 | 5 |

Example 9: Dehydration Reaction of Glycerin

The preparation of acrolein by dehydration of glycerin was carried out by using a continuous flow fixed bed reactor. After installing the continuous flow fixed bed reactor in an electric furnace, about 0.1 to about 0.4 g of the catalyst prepared in Preparation Example 9 was put in the reactor. After elevating the temperature of the reactor to about 290° C. with flowing nitrogen and air, carrier gas, respectively with the velocity of 10 mL/min, the temperature was maintained for a period of time for maintaining the steady state of the reaction line.

Subsequently, glycerin aqueous solution (28.08 wt % in $H_2O$; 7.1 mol %) was introduced to the reactor with the velocity of 1.2 mL/hr to the catalyst and the dehydration reaction of glycerin was carried out. At this time, the gas hourly space velocity (GHSV) was 5409/hr.

The dehydration reaction of glycerin was carried out at the temperature of about 290° C. under atmospheric pressure for about 1 to 5 hrs, and the product obtained after the reaction included not only acrolein, the main product, but also by-products such as hydroxyacetone (acetol) and allyl alcohol and unreacted glycerin. During the reaction proceeded, the reaction product was sampled for 10 mins once an hour and analyzed by gas chromatography at regular intervals.

Examples 10 to 14 and Comparative Examples 2 to 3: Dehydration Reaction of Glycerin The dehydration reaction of glycerin was carried out according to the same method as in Example 9, except that the catalyst was changed as disclosed in the following Table 2.

TABLE 2

| | Catalyst |
|---|---|
| Example 9 | $Zr_{0.9}Ag_{0.1}W_{0.1}(H_yPO_4)_2$ of Preparation Example 9 |
| Example 10 | $Zr_{0.9}Ca_{0.1}W_{0.1}(H_yPO_4)_2$ of Preparation Example 10 |
| Example 11 | $Zr_{0.9}Nb_{0.1}W_{0.1}(H_yPO_4)_2$ of Preparation Example 11 |
| Example 12 | $Zr_{0.9}Mg_{0.1}W_{0.1}(H_yPO_4)_2$ of Preparation Example 12 |
| Example 13 | $Zr_{0.9}Ca_{0.01}W_{0.1}(H_yPO_4)_2$ of Preparation Example 13 |
| Example 14 | $Zr_{0.9}K_{0.01}W_{0.1}(H_yPO_4)_2$ of Preparation Example 14 |
| Comparative Example 2 | $BPO_4$ |
| Comparative Example 3 | $ZrP_2O_7$ |

Experimental Example: Evaluation on Dehydration of Glycerin

Conversion ratio of glycerin, selectivity of acrolein, selectivity of acetol, and yield of acrolein according to the glycerin hydration reactions of Examples 1 to 14 and Comparative Examples 1 to 3 were calculated by the following Equations 1 to 3, and the results are listed in the following Table 3.

Conversion ratio of glycerin (%)={(mole of glycerin provided−mole of unreacted glycerin)/(mole of glycerin provided)}*100    [Equation 1]

Selectivity of acrolein (%)={(mole of acrolein produced/(mole of glycerin provided−mole of unreacted glycerin)}*100    [Equation 2]

Selectivity of acetol (%)={(mole of acetol produced)/(mole of glycerin provided−mole of unreacted glycerin)}*100    [Equation 3]

Yield of acrolein (%)={(mole of acrolein produced)/(mole of glycerin provided)}*100    [Equation 4]

TABLE 3

| | Conversion ratio of glycerin [%] | Selectivity of acrolein [%] | Selectivity of acetol [%] | HA/AC[(1)] | Yield of acrolein [%] |
|---|---|---|---|---|---|
| Example 1 | 60.53 | 69.98 | 8.35 | 0.11 | 42.36 |
| Example 2 | 43.24 | 64.90 | 9.33 | 0.14 | 28.06 |
| Example 3 | 38.55 | 64.85 | 10.05 | 0.15 | 25.00 |
| Example 4 | 42.72 | 66.91 | 3.54 | 0.05 | 28.58 |
| Example 5 | 51.47 | 56.94 | 9.44 | 0.17 | 29.31 |
| Example 6 | 37.83 | 65.61 | 7.74 | 0.12 | 24.82 |
| Example 7 | 66.28 | 69.76 | 3.81 | 0.05 | 46.24 |
| Example 8 | 51.92 | 72.66 | 8.56 | 0.12 | 37.73 |
| Example 9 | 93.79 | 55.84 | 6.66 | 0.12 | 52.37 |
| Example 10 | 33.70 | 57.68 | 14.38 | 0.24 | 19.44 |
| Example 11 | 22.09 | 56.11 | 10.81 | 0.19 | 12.40 |
| Example 12 | 24.93 | 58.44 | 12.75 | 0.22 | 14.57 |
| Example 13 | 96.13 | 71.59 | 11.52 | 0.16 | 68.82 |
| Example 14 | 45.55 | 63.30 | 10.11 | 0.16 | 29.47 |
| Comparative Example 1 | 1.60 | 12.36 | 10.31 | 0.83 | 0.20 |
| Comparative Example 2 | 10.49 | 14.39 | 11.71 | 0.81 | 1.51 |
| Comparative Example 3 | 3.94 | 28.55 | 5.01 | 0.17 | 1.12 |

[(1)]HA/AC: ratio of selectivity of acetol (HA) to selectivity of acrolein (AC)

Referring to Table 2, it is recognized that the catalysts according to one embodiment of the present invention can provide higher yield of acrolein than existing boron phosphate ($BPO_4$) and zirconium phosphate ($ZrP_2O_7$) catalysts and show very high acrolein selectivity. It is also recognized that the catalysts according to one embodiment of the present invention do not increase the amount of acetol (hydroxyacetone), a major by-product, produced in spite of its high glycerin conversion ratio, and have the HA/AC value equal to or less than existing catalysts.

The invention claimed is:

1. A catalyst for dehydration of glycerin represented by the following Chemical Formula 1:

$Zr_xA_n(H_yPO_m)_z$    [Chemical Formula 1]

in Chemical Formula 1, A is one or more atoms selected from the group consisting of B, W, V, Ca, K, Mg, Sr, Ag, Ni, Zn, Fe, Sn, and Nb; and x, n, m, y, and z represent ratios of atoms or atom groups, wherein x is 0.1 to 6, n is 0.01 to 8, y is 0.1 to 10, m is 1 to 5, and z is 1 to 12.

2. The catalyst for dehydration of glycerin according to claim 1, wherein n is 0.01 to 0.3, m is 4, x is 0.5 to 1, y is 1 to 3, and z is 1 to 5.

3. The catalyst for dehydration of glycerin according to claim 1, wherein the catalyst represented by Chemical Formula 1 is a compound represented by Chemical Formula 2:

$Zr_xA^1_{n1}(H_yPO_4)_z$    [Chemical Formula 2]

in Chemical Formula 2, x is 0.5 to 1, $A^1$ is W or Zn, n1 is 0.01 to 0.3, y is 1 to 3, and z is 1 to 5.

4. The catalyst for dehydration of glycerin according to claim 1, wherein the catalyst represented by Chemical Formula 1 is a compound represented by Chemical Formula 3:

$Zr_xA^2_{n2}W_{n3}(H_yPO_4)_z$    [Chemical Formula 3]

in Chemical Formula 3, x is 0.5 to 1, $A^2$ is B, V, Ca, K, Mg, Ag, Zn, Fe, or Nb, y is 1 to 3, z is 1 to 5, and n2 and n3 are independently a rational number between 0.001 to 0.2 and the sum of n2 and n3 is 0.01 to 0.3.

5. The catalyst for dehydration of glycerin according to claim 1, wherein the catalyst represented by Chemical Formula 1 is a compound represented by Chemical Formula 4:

$Zr_xA^3_{n4}A^4_{n5}A^5_{n6}(H_yPO_4)_z$    [Chemical Formula 4]

in Chemical Formula 4, x is 0.5 to 1, $A^3$ to $A^5$ are independently W, Zn, or Fe, y is 1 to 3, z is 1 to 5, and n4 to n6 are independently a rational number between 0.001 to 0.2 and the sum of n4, n5, and n6 is 0.01 to 0.3.

6. The catalyst for dehydration of glycerin according to claim 1, wherein the catalyst represented by Chemical Formula 1 is $ZrB_{0.1}W_{0.1}(H_yPO_4)_{2.2}$, $Zr_{0.9}Fe_{0.1}W_{0.1}Zn_{0.02}(H_yPO_4)_2$, $ZrZn_{0.1}(H_yPO_4)_2$, $Zr_{0.9}Ag_{0.1}W_{0.1}(H_yPO_4)_2$, or $Zr_{0.9}Ca_{0.01}W_{0.1}(H_yPO_4)_2$, and y is 1 to 3.

7. A preparation method of the catalyst for dehydration of glycerin, including the steps of mixing one or more precursors selected from the group consisting of the precursors of B, W, V, Ca, K, Mg, Sr, Ag, Ni, Zn, Fe, Sn, and Nb, a zirconium precursor, and a phosphate compound, and precipitating a catalyst represented by Chemical Formula 1 therefrom:

$$Zr_xA_n(H_yPO_m)_z \qquad \text{[Chemical Formula 1]}$$

in Chemical Formula 1, A is one or more atoms selected from the group consisting of B, W, V, Ca, K, Mg, Sr, Ag, Ni, Zn, Fe, Sn, and Nb; and x, n, m, y, and z represent ratios of atoms or atom groups, wherein x is 0.1 to 6, n is 0.01 to 8, y is 0.1 to 10, m is 1 to 5, and z is 1 to 12.

8. The preparation method of the catalyst for dehydration of glycerin according to claim 7, wherein the step of precipitating the catalyst includes the process of stirring the mixture including one or more precursors selected from the group consisting of the precursors of B, W, V, Ca, K, Mg, Sr, Ag, Ni, Zn, Fe, Sn, and Nb, a zirconium precursor, and a phosphate compound at the temperature of 25 to 200° C.

9. The preparation method of the catalyst for dehydration of glycerin according to claim 7, wherein the mixture is stirred for 3 to 48 hrs.

10. The preparation method of the catalyst for dehydration of glycerin according to claim 7, further including the step of washing the precipitated catalyst with an alcohol after the step of precipitating the catalyst.

11. A preparation method of acrolein, including the step of dehydrating glycerin in the presence of the catalyst for dehydration of glycerin of claim 1.

* * * * *